United States Patent [19]

Possis

[11] 3,997,923
[45] Dec. 21, 1976

[54] HEART VALVE PROSTHESIS AND SUTURING ASSEMBLY AND METHOD OF IMPLANTING A HEART VALVE PROSTHESIS IN A HEART

[75] Inventor: Zinon C. Possis, Edina, Minn.
[73] Assignee: St. Jude Medical, Inc., Columbia Heights, Minn.
[22] Filed: Apr. 28, 1975
[21] Appl. No.: 572,001

[52] U.S. Cl. .......................................... 3/1.5; 3/1; 128/334 R
[51] Int. Cl.² ................................................ A61F 1/22
[58] Field of Search ............ 3/1, 1.5, 1.912–1.913, 3/13; 128/334 R, 334 C

[56] References Cited
UNITED STATES PATENTS

| | | | |
|---|---|---|---|
| 2,714,721 | 8/1955 | Stone | 3/1 |
| 3,074,407 | 1/1963 | Moon et al. | 3/1 X |
| 3,458,870 | 8/1969 | Stone | 3/13 |
| 3,781,969 | 1/1974 | Anderson | 3/1.5 X |
| 3,818,512 | 6/1974 | Shersher | 3/1.912 |
| 3,903,548 | 9/1975 | Nakib | 3/1.5 |

FOREIGN PATENTS OR APPLICATIONS

| | | | |
|---|---|---|---|
| 1,180,087 | 10/1964 | Germany | 3/1.5 |

OTHER PUBLICATIONS

"The In Vivo Comparison of Hemodynamic Function of Ball, Disk, and Eccentric Monocusp Artificial Mitral Valves" by R. W. M. Frater et al.
*Prosthetic Heart Valves* (Book) by L. A. Brewer, Charles C. Thomas–Publisher 1969, pp. 262–277.

*Primary Examiner*—Ronald L. Frinks
*Attorney, Agent, or Firm*—L. Paul Burd; William A. Braddock; Richard O. Bartz

[57] ABSTRACT

A heart valve prosthesis removably mounted on a suturing assembly. The suturing assembly has an annular sleeve carrying a fabric collar. Sutures secure the collar to heart tissue. The heart valve has a base that is removably mounted on the annular sleeve. The suturing assembly is initially secured to the heart tissue. The heart valve base is then attached to the sleeve and locked in place. If a replacement valve is necessary, the heart valve prosthesis is removed from the sleeve without detaching the suturing assembly from the heart tissue. A new heart valve prosthesis is then mounted on the suturing assembly.

35 Claims, 13 Drawing Figures

U.S. Patent  Dec. 21, 1976  Sheet 1 of 3  3,997,923
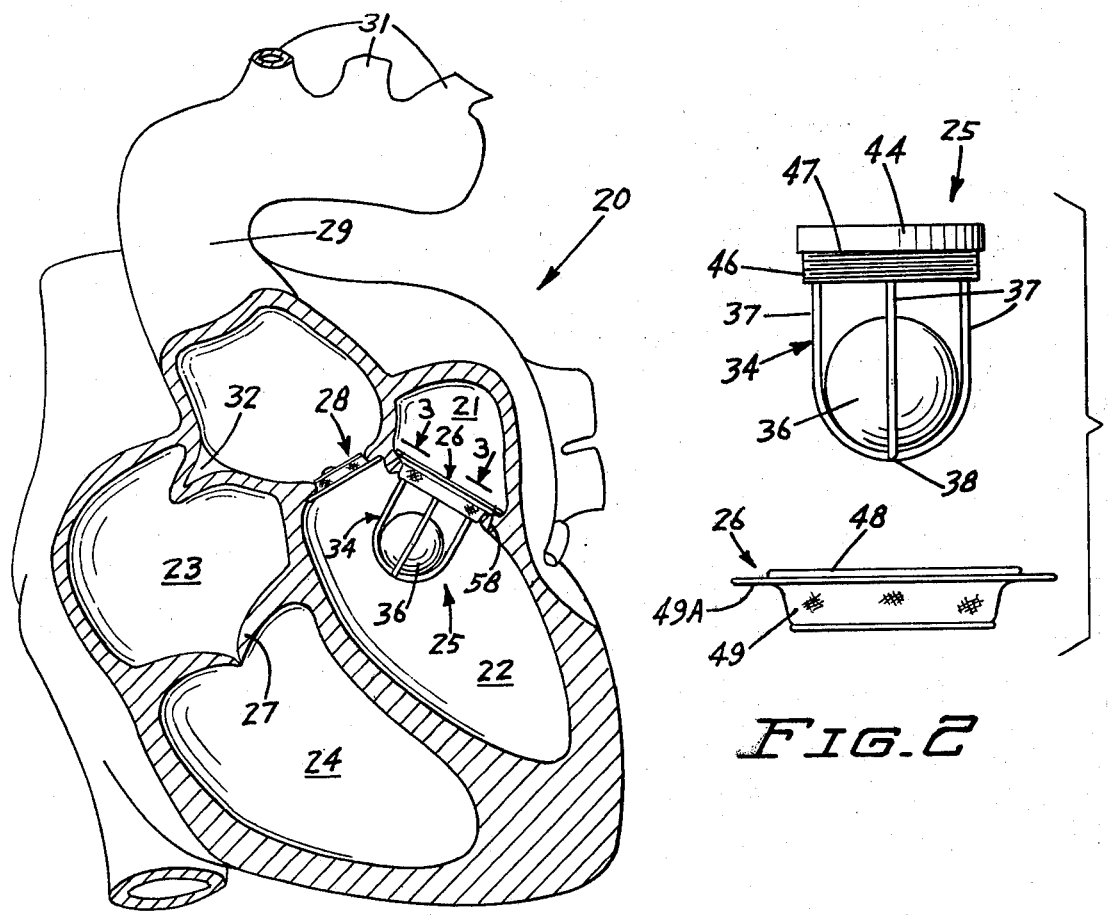
FIG.2
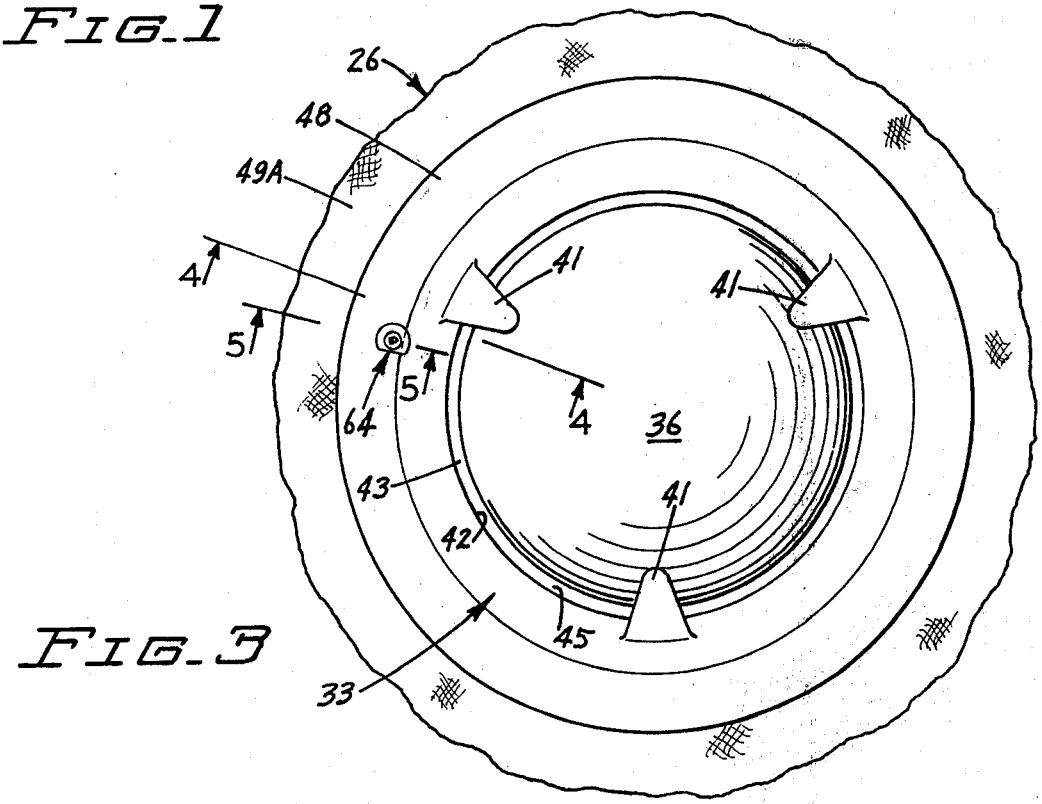
FIG.1
FIG.3

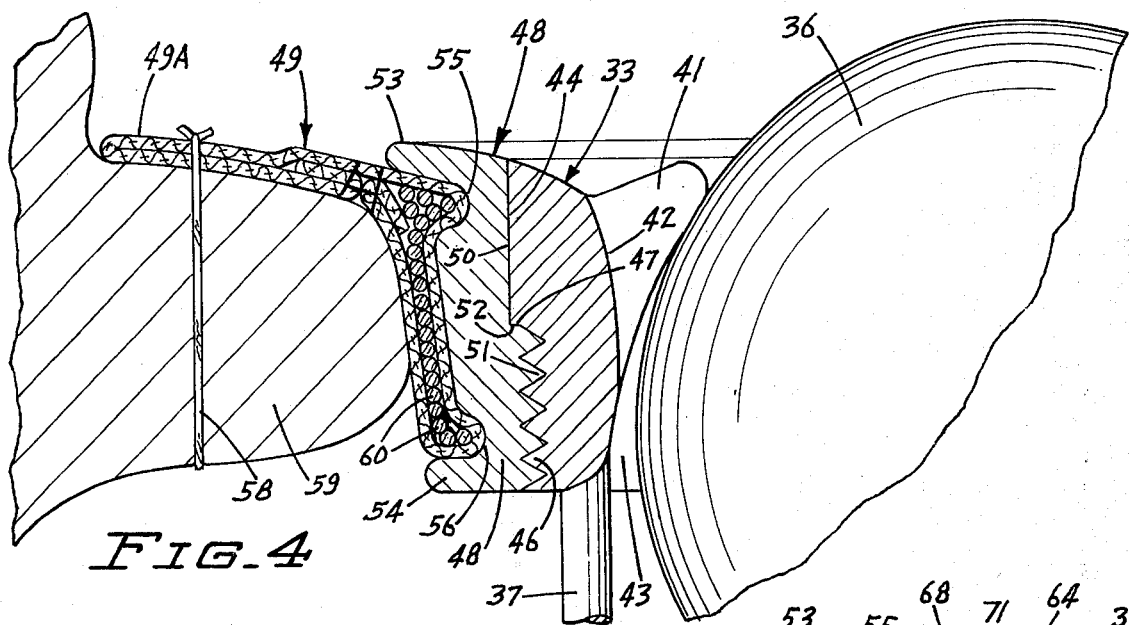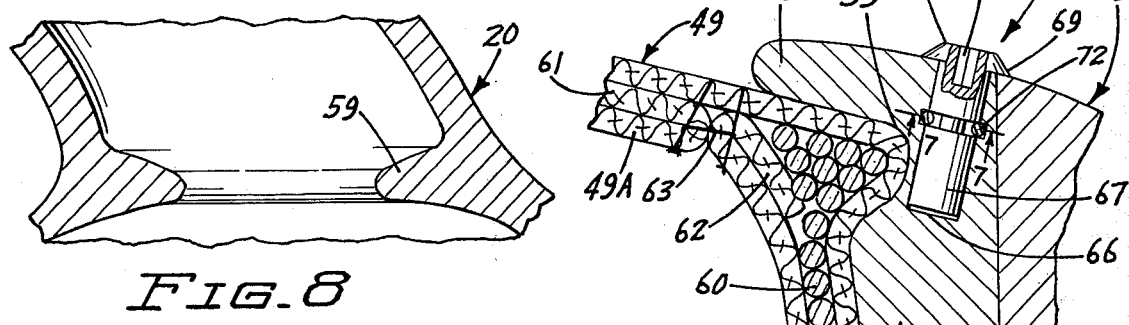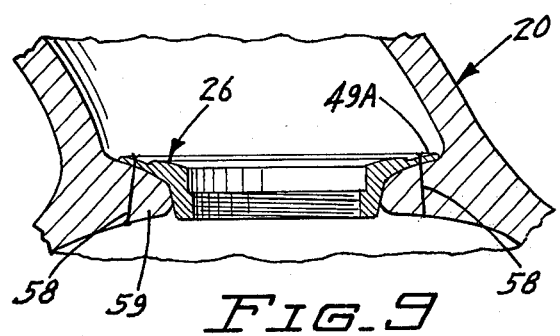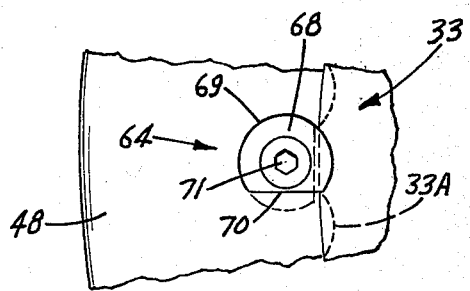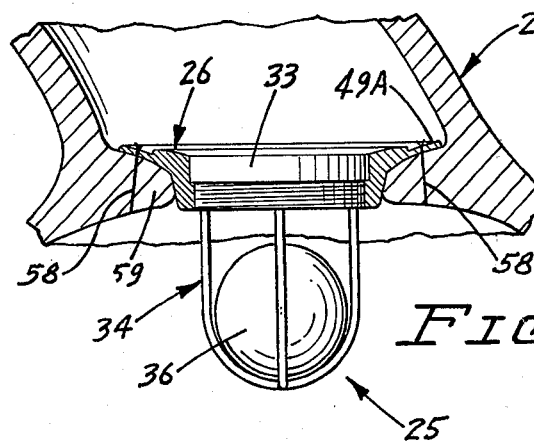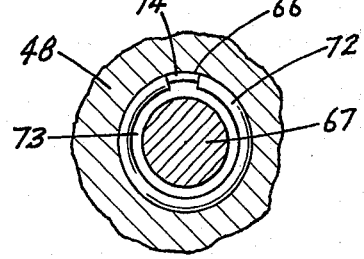

HEART VALVE PROSTHESIS AND SUTURING ASSEMBLY AND METHOD OF IMPLANTING A HEART VALVE PROSTHESIS IN A HEART

BACKGROUND OF THE INVENTION

Sewing rings or suturing members are used to attach heart valve prostheses to heart tissue. Sutures connect the sewing ring to the tissue. The sewing rings are made of biologically inert materials that are compatible with blood and heart tissue. Many sewing rings have fabric covers which permit tissue ingrowth whereby the sewing rings are firmly attached to the heart tissue. The tissue ingrowth does not allow the sewing ring to be readily removed from the heart tissue without cutting additional heart tissue. Examples of suturing members for heart valves are shown in U.S. Pat. Nos. 3,099,016; 3,491,376; and 3,763,548.

Prosthetic heart valves have been proposed which are attached to the heart tissue with clamp and hook-like structures. These valves are known as sutureless heart valves. Examples of heart valve prostheses using sutureless fixations are shown in U.S. Pat. Nos. 3,143,742; 3,546,710; and 3,574,865. Replacement of the valve cannot be accomplished unless the valve structure is disassembled or the valve is removed with a portion of the heart tissue remaining attached to the valve structure.

The normal heart valve prosthesis must be reliable in use over an extended period of time. The valving member of a functioning heart valve prosthesis completes 40 million cycles in each year of operation. After a period of time, many heart valve prostheses malfunction and must be replaced with a new heart valve prosthesis. Changes in the condition of the patient and heart of the patient may require a new heart valve prosthesis or a heart valve prosthesis of a different design. It may be desirable that a new heart valve prosthesis of a new design be used in lieu of a heart valve prosthesis operating in the heart.

SUMMARY OF THE INVENTION

The invention relates to a heart valve prosthesis and suturing assembly wherein the heart valve can be removed from the suturing assembly after the suturing assembly has been attached to the heart tissue. A new heart valve prosthesis of the same or different type, i.e., ball, disc, poppet or torus valve, can be mounted on the suturing assembly attached to the heart tissue. Broadly, the invention is directed to a suturing structure attachable to living tissues for releasably holding a device such as an implantable device, including a heart valve prosthesis.

The heart valve prosthesis has a base with a passage for permitting the flow of blood through the base. A movable valving element is retained on the base to permit one-way flow of blood through the passage. The suturing assembly has means for releasably accommodating the base whereby the base can be removed from the suturing assembly after the suturing assembly has been attached to the heart tissue. Lock means associated with the the suturing assembly and base are used to hold the base in a fixed assembled relation with the suturing assembly. The suturing assembly and base have coacting releasable structures, such as cooperating threads, tongue and groove structures and the like, which mount the base on the suturing assembly. The threads can be four start threads whereby the base can be quickly attached to the suturing assembly and the valving member circumferentially orientated to provide a blood flow in a desired direction away from the valve.

The invention also includes the method of implanting a heart valve prosthesis in a heart, circumferentially orientating the valve member, and replacing the heart valve prosthesis at a subsequent time. The natural heart valve is removed from the heart, leaving a small annular valve rim or remnant on the heart wall. The suturing assembly is then placed in the opening created by removal of the natural heart valve and attached to the annular valve rim. This is accomplished with attaching means, as sutures, clips or tissue adhesives. The heart valve is then mounted on the suturing assembly. When a disc-type valve is used, the valve base and disc are circumferentially orientated or positioned away from the heart tissue and calcifications which can interfere with the blood flow and free movement of the disc. During the healing process, heart tissue grows into the suturing assembly to form a permanent mechanical union. The heart valve prosthesis can be replaced without damaging the union between the suturing assembly and the heart tissue nor damaging the new heart valve prosthesis.

An object of the invention is to provide a suturing assembly adapted to releasably accommodate a device, as a heart valve prosthesis, in a manner so as to permit the device to be removed from the suturing assembly after the suturing assembly has been attached to living tissue. A further object of the invention is to provide a suturing assembly adapted to releasably hold heart valve prostheses of different designs whereby heart valve prostheses of different designs and types can be interchanged by the surgeon. Another object of the invention is to provide a heart valve prosthesis that can be attached to a suturing assembly in selected circumferential positions so that the blood flow direction away from the valve can be controlled and the moving valving means positioned away from heart tissue and calcifications that may interfere with movement of the valving member. Another object of the invention is to provide a heart valve prosthesis with structure which allows a malfunctioning heart valve prosthesis to be replaced with a new heart valve prosthesis without removing the structure used to attach the heart valve prosthesis to the heart tissue. Yet a further object of the invention is to provide a heart valve prosthesis and a method of implanting the heart valve prosthesis which can be implanted in the heart with a minimum of danger of damaging the valve structure. Another object of the invention is to provide a method of implanting a heart valve prosthesis in a human heart wherein a suturing assembly is initially secured to the heart tissue independent of the heart valve prosthesis and the heart valve prosthesis mounted on the suturing assembly after it is connected to the heart tissue. Yet another object of the invention is to provide a method wherein a heart valve prosthesis can be replaced without removing the suturing member used to hold the heart valve prosthesis in operative relation with the heart tissue. Other objects and advantages of the heart valve prosthesis and suturing assembly are set out and apparent from the following description of the invention.

IN THE DRAWINGS

FIG. 1 is a schematic illustration, partly in section, of a human heart having a heart valve prosthesis mounted on a suturing assembly connected to heart tissue;

FIG. 2 is an exploded side elevational view of the heart valve prosthesis and suturing assembly;

FIG. 3 is an enlarged sectional view taken along line 3—3 of FIG. 1;

FIG. 4 is an enlarged sectional view taken along line 4—4 of FIG. 3;

FIG. 5 is in enlarged sectional view taken along line 5—5 of FIG. 3;

FIG. 6 is a top plan view of FIG. 5;

FIG. 7 is an enlarged sectional view taken along line 7—7 of FIG. 5;

FIG. 8 is a sectional view of a portion of a human heart with the natural heart valve removed;

FIG. 9 is a view similar to FIG. 8 with a suturing assembly stitched to heart tissue;

FIG. 10 is a view similar to FIG. 9 showing a heart valve prosthesis mounted on the suturing assembly;

DESCRIPTION OF PREFERRED EMBODIMENT

Figure 11:
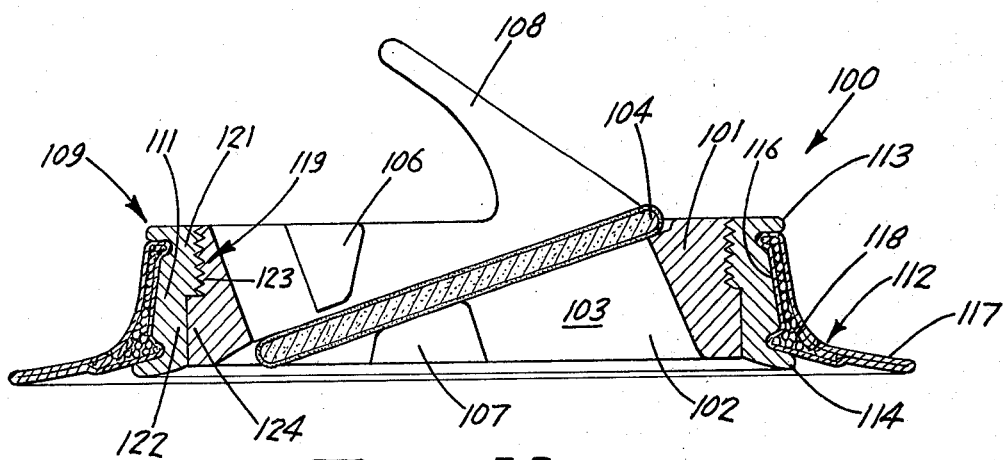
FIG. 11 is a side elevational view in section of a first type of disc heart valve removably mounted on the suturing assembly of the invention.
Figure 12:
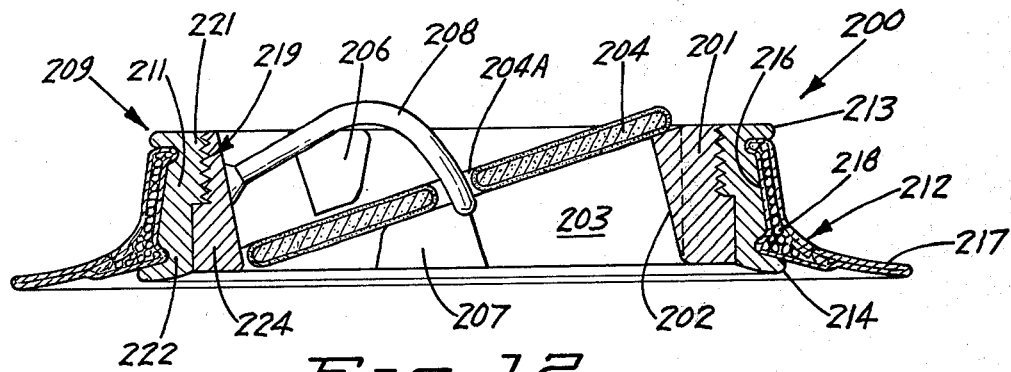
FIG. 12 is a side elevational view in section of a second type of disc heart valve removably mounted on the suturing assembly of the invention.
Figure 13:
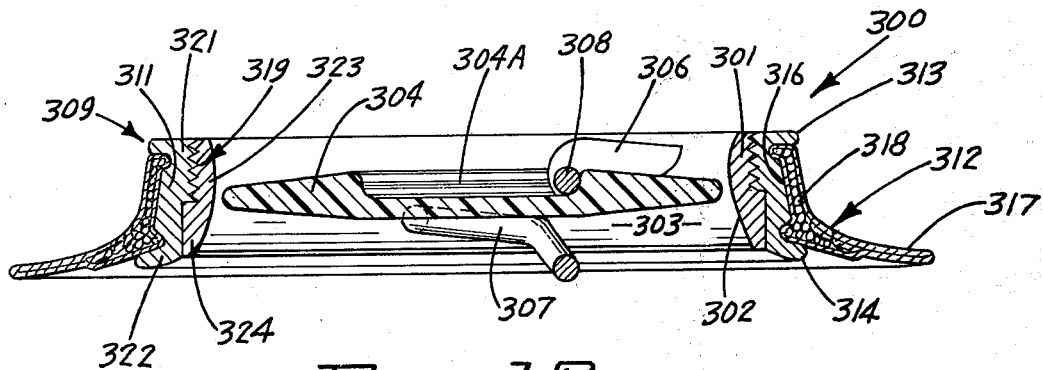
FIG. 13 is a side elevational view of a third type of disc heart valve removably mounted on the suturing assembly of the invention.

Referring to FIG. 1, there is shown a diagram of a human heart 20 with the suturing assembly 26 of the invention carrying a ball-type heart valve prosthesis 25. Other types of heart valve prostheses, such as shown in FIGS. 11, 12 and 13, can be releasably mounted on the suturing assembly 26 with suitable modification to the base or ring parts of the valves. Examples of other heart valves are shown in U.S. Pat. Nos. 3,438,394; 3,737,919; 3,824,629 and 3,825,956. Heart 20 has a left atrium 21 and a left ventricle 22. the right atrium 23 is separated from the right ventricle 24 with a mitral valve 27. An aortic valve prosthesis 28 is located between the left ventricle 22 and the aorta 29. Prosthesis 28 is located inwardly of the coronary arteries 32. The aorta 29 leads to a plurality of arteries 31.

Referring to FIG. 2, valve 25 has an annular base, ring or housing 33 having a passage 43 for allowing blood to flow through the base. An open cage 34 is secured to the base 33. A spherical valving member or ball 36 is located within the cage 34 and moves relative to base 33 to open and close passage 43. Cage 34 comprises three rod members 37 having ends secured to one side of base 33. The opposite ends of the rod members 37 curve inwardly and are secured together at 38 along the central axis of the passage 43.

Referring to FIG. 3, base 33 has inwardly directed projections or legs 41 on the blood inlet side of the base that engage separate portions of ball 36 when the ball 36 is in the closed position. Cage 34 and legs 41 are retaining means that hold the ball 36 in free-floating relationship with the base 33. Base 33 has an inside annular wall 44 surrounding the passage 43. When ball 36 is in the closed position, there is a slight annular space 45 between the outer peripheral surface of the ball and the adjacent inside wall 42. The annular space 45 allows limited reverse or back flow of blood through the passage 43 and prevents the ball 36 from being held on the base 33. Ball 36 is free to randomly rotate in base 33 and cage 34, thereby avoiding localized sites of wear.

Referring to FIG. 4, base 33 has an outside cylindrical wall 44 and a threaded cylindrical section 46. An inwardly directed annular shoulder 47 is located between wall 44 and threaded section 46. The threaded section 46 has a diameter smaller than the diameter of wall 44.

The materials of base 33 and ball 36 are wear resistant and compatible with blood, body fluids and tissues. Examples of these materials include plastics, as polycarbonates, alumina ceramics, metal such a titanium, and silicone alloyed pyrolytic carbon coated substrates. Pyrolytic carbon materials are disclosed as usable in heart valves in U.S. Pat. Nos. 3,546,711; 3,737,919 and 3,825,956.

Suturing assembly 26 has an annular member or sleeve indicated generally at 48 carrying a collar 49. Sleeve 48 is a rigid member of metal, plastic or like material. Collar 49 has an outwardly directed annular flexible flange 49A. When suturing assembly 26 is used in the aortic position, flange 49A can be omitted so collar 49 has an annular cylindrical shape. Collar 49 includes a fabric cover, as "Teflon" or "Dacron" cloth. The cloth is biologically inert and does not deteriorate with time. The cloth is preferably an interlaced or knitted fabric having spaces into which living neointima tissue grows to form a permanent mechanical union between the cloth and the tissue independent of sutures applied by the surgeon. The materials of the suturing assembly 26 are sterilizable, biologically inert, non-irritating, non-pyrogenic and non-toxic to body fluids and tissue.

Sleeve 49 has an inside cylindrical wall 50 and a threaded section 51 adapted to engage wall 44 and threaded section 46 of base 33. An annular shoulder 52 is located between the wall 50 and threaded section 51. The shoulder 52 engages shoulder 47 to fix the assembled position of base 33 on the sleeve 48. Threaded sections 46 and 51 have a plurality of screw threads. Preferably the threads are four start threads whereby the base 33 can be mounted on the sleeve 48 in four positions. The number, size and type of threads can vary and still achieve a releasable connection between the base 33 and sleeve 48. Other types of coupling structures, as tongue and grooves, splines, projections, dimples and recesses and the like, can be used to mount the valve base 33 on sleeve 48. Base 33 and sleeve 48 have coacting cooperating means, i.e., threads 46 and 48, which permit the removal of the heart valve prosthesis after the suturing assembly has been applied to the heart tissue. This means also permits circumferential positioning or orientation of the valve base on the suturing assembly.

Sleeve 48 has outwardly directed upper and lower annular flanges 53 and 54. An upper, outwardly open groove 55 is located adjacent flange 53. A similar lower, outwardly open groove 56 is located adjacent the inside of flange 54. Collar 49 has suture receiving porous fabric member or cloth 57 and is mounted on the sleeve 48. Connecting means, as sutures 58, are used to attach the collar 49 to the heart tissue 59. The connecting means can be clips or tissue adhesive. Fabric member 57 has a portion located between flanges 53 and 54. A plurality of cords, surgical ties or strings, or threads 60 are wrapped around the member 57 to hold the member 57 on the sleeve 48. A plastic sleeve may be used to hold fabric member 57 on sleeve 48. Examples of plastic sleeves used in suturing members are disclosed in U.S. Pat. Nos. 3,396,409; 3,763,548 and 3,824,629. One or more cords hold a portion of the fabric member 57 in groove 55. Additional cords hold another portion of the fabric member 57 in groove 56. The fabric member 57 is thereby held in a fixed position on sleeve 48. The cords 60 hold the upper and lower portions of the fabric member 57 in engagement with flanges 53 and 54. The fabric member 57 has turned ends 61 and 62 that are joined together with suitable stitches 63. Stitches 63 also hold a portion of the fabric member 57 adjacent the outside of cords 60.

Referring to FIGS. 3, 5, 6 and 7, there is shown a releasable lock means indicated generally at 64 for holding the base 33 in assembled relation with sleeve 48. Releasable lock means 64 includes a bore 66 in the sleeve 48 adjacent the lower or inflow end of the sleeve 48. A rotatable body 67 is located in the bore 66. An enlarged head 68 integral with the outer end of body 67 has a lip 69 of a length sufficient to extend over a portion of the base 33, as shown in FIG. 5. Head 68 has a flat side 70 used to release the base 33 from sleeve 48. The central part of head 68 has an inwardly directed socket 71 having a non-circular shape for accommodating a tool used to rotate the head. When the head 68 is rotated approximately 90°, as shown in broken lines in FIG. 6, the lip 69 is moved from the base 33. The base 33 can then be rotated to disassemble the base from the sleeve 48.

The body 67 is held in assembled relation with the sleeve 48 with a snap ring 72. As shown in FIG. 7, body 67 has a annular groove 73. The sleeve 48 has an annular groove 74. Grooves 73 and 74 are aligned with each other and accommodate the snap ring 72. When the body 67 is inserted into bore 66, the snap ring 72 is contracted until grooves 73 and 74 are aligned. The snap ring 72 will then expand to hold the body 67 in a fixed longitudinal position in the bore 66. The snap ring 72 permits the body 67 to be rotated. The body 67 has a firm frictional fit with bore 66 so that it cannot inadvertently rotate without the use of a tool.

Other types of releasable locks can be used to hold the base 33 in a fixed position on sleeve 48. Body 67 can be provided with threads that cooperate with threads on sleeve 48 to hold the lock on sleeve 48. Base 33 can be provided with serrations or arcuate recesses, shown in broken lines at 33A in FIG. 6, for accommodating the side of head 69 to lock base 33 in a fixed position on sleeve 48. Alternatively, base 33 can have grooves in wall 44 to accommodate a part of body 67 mounted in a bore in sleeve 48 to lock the base 33 on sleeve 48.

Referring to FIG. 11, there is shown a disc-type heart valve prosthesis indicated generally at 100 carrying a removable suturing assembly 109. Valve 100 is pivoted disc-type heart valve of the type shown in U.S. Pat. Nos. 3,476,143 and 3,737,919. Valve 100 has an annular base, ring or housing 101 having an inside annular wall 102. Annular wall 102 forms a passage 103 through base 101. A valving member shown as a free floating disc 104 is movably positioned in passage 103 to control the flow of blood through the passage. The movement of disc 104 is controlled by pivot members 106 and 107 secured to base 101 and projected into passage 103. FIG. 11 shows a first pair of pivot members 106 and 107. A second pair of pivot members (not shown) is mounted on base 101 and faces the members 106 and 107. The disc 104 cooperates with the two pairs of pivot members during its opening and closing movements. Side arms or projections 108 extend upwardly from the base 106 to retain the disc 104 in operative assembled relation with base 101.

Suturing assembly 109 is mounted on the outside of base 101 and is used to attach the base to the heart tissue. Suturing assembly 109 has an annular sleeve or ring member 111 carrying a flexible fabric collar 112. Sleeve 111 has a pair of annular outwardly directed flanges 113 and 114 and an outwardly open groove 116. A cover 117 is located in the groove and is retained therein with a plurality of cords 118. The cover 117 has an outwardly directed annular flexible flange for accommodating sutures or connecting structures to attach the cover 117 to the heart tissue. The flange of the cover can be eliminated whereby the suturing member can be attached to heart tissue to place the valve in the aortic position.

The base 101 and sleeve 111 have coacting cooperating means indicated generally at 119 which permit the removal of the heart valve prosthesis from the suturing assembly after the suturing assembly has been attached to the heart tissue. The coacting cooperating means 119 permits the circumferential or angular positioning of the valve base 101 relative to suturing sleeve 111. This allows the surgeon to change the orientation of the disc 104 and the direction of the flow of blood in the blood receiving chamber. One type of coacting cooperating means, shown in FIG. 11, includes a threaded annular section 121 and a cylindrical section 122 on sleeve 111. The base 101 has an external threaded section 123 and cylindrical section 124 which are complementary to threaded sections 121 and 122 whereby the base 101 can be attached to the sleeve 111. Preferably, the threads are four start threads whereby the base 101 can be mounted on sleeve 111 in four separate positions. The number, size and type of the threads can vary. The plurality of start threads enables the surgeon to circumferentially orient the valve base and its disc in the heart so that the blood, as it flows through the valve, is deflected in a desired direction in the heart.

The base 101 is preferably locked on sleeve 111 after the base has been attached to the sleeve. A releasable lock, as indicated generally at 64 in FIGS. 3, 5, 6 and 7, can be used to achieve this purpose. Other types of locking structures can be used to hold the base 101 in a fixed position on sleeve 111. The suturing assembly 109 is constructed in a manner to receive other types of valves such as ball valve 25 shown in FIGS. 1 and 2 and the disc valves shown in FIGS. 12 and 13.

Referring to FIG. 12, heart valve 200 has an annular base or housing 201 having an inside annular wall 202. The annular wall defines a passage 203 through base 201. A valving member or disc 204 is operatively positioned in passage 203 to control the flow of blood through passage 203. The disc 204 cooperates with pivot members 206 and 207 during its movements between its open and closed positions. The pivot members 206 and 207 are secured to the base and extend into passage 203. A second pair of pivot members (not shown) located opposite the pivot members 206 and 207 function with pivot members 206 and 207 to control the pivotal movement of disc 204. A retaining member 208 in the shape of a curved rod holds the disc 204 in its moving operative assembled relation with the base 201. The retaining means is secured at one end to the base 201. The opposite end of retaining means 208 projects through a center hole 204A in disc 204. The valve 200 is of the type shown in U.S. Pat. Nos. 3,825,956 and 3,825,957.

Suturing assembly 209 is identical in construction with suturing members 109 and 309. The suturing assembly 209 has annular ring or sleeve 211 carrying a flexible fabric collar 212. Collar 212 is located in a groove 216 and between flanges 213 and 214 which project outwardly from sleeve 211. Collar 212 has a fabric cover 217 having an outwardly directed flexible annular flange. A plurality of cords 218 hold the cover 217 in assembled relation on the sleeve 211 between the flanges 213 and 214.

Coacting cooperating means indicated generally at 219 releasably connect the base 201 with sleeve 211. The coacting cooperating means 219 comprise structure in the form of a threaded section 221 and a cylindrical section 222 on sleeve 211. The outside annular wall of base 201 has a threaded section 223 and a cylindrical section 224 that are complementary to and cooperate with sections 221 and 222 of sleeve 211 to releasably mount the base 201 on sleeve 211. Preferably, the threads of sections 221 and 223 are four start threads whereby the base 201 can be mounted on the sleeve 211 in four positions. The number, size and type of threads can vary, permitting additional adjustment of the base relative to the sleeve. The cooperating thread structures between base 201 and sleeve 211 permit the surgeon to circumferentially orient the base 201 and disc 204 in the heart so that the direction of flow of blood through passage 203 can selected by the surgeon to be most advantageous to the patient.

Referring to FIG. 13, there is shown a pivoted discoid heart valve of the type shown in U.S. Pat. No. 3,824,629. Valve 300 has an annular base, ring or housing 301 having an inside annular wall 302. Annular wall 302 surrounds a passage 303 through base 301. A poppet or disc 304 is operatively positioned in passage 303 and is used to control the flow of blood through the passage. The disc 304 cooperates with pivot members 306 and 307 located on opposite sides of the disc during its opening and closing movements to control the movement of disc 304. The disc 304 has a circular center top recess 304A which receives a center portion or projection 308 of the pivot member 306 to retain the disc in operative moving assembled relation with the base 301.

A suturing assembly indicated generally at 309 is removably mounted on the outside of base 301. Suturing assembly 309 comprises an annular ring or sleeve 311. A suture receiving collar 312 is mounted on the outside of sleeve 311. The sleeve 311 has outwardly directed annular flanges 313 and 314 located on opposite sides of an annular outwardly open groove 316. The The collar 312 comprises a fabric cover 317. A plurality of cords 318 are wrapped around inside portions of the cover 317 to hold the cover in assembled relation with sleeve 311. A plastic sleeve can be used in lieu of cords 318. Examples of annular or sleeve holding means are disclosed in U.S. Pat. Nos. 3,396,409; 3,763,548 and 3,824,629. Cover 317 has an outwardly directed annular flange adapted to receive sutures to attach the suturing assembly to the heart tissue. The flange can be omitted whereby the collar will have a shape similar to the suturing collar shown in U.S. Pat. No. 3,824,629.

Coacting cooperating means indicated generally at 319 mount the base 301 on sleeve 311. The coacting cooperating means comprise the inside portion of sleeve 311 which includes a threaded section 321 and a cylindrical section 322. The base 301 has an annular outside threaded section 323 and a cylindrical section 324 which are complementary to and cooperate with sections 321 and 322 to mount the base 301 on sleeve 311. Preferably, the cooperating threads of sections 321 and 323 are four start threads so that the base 301 can be mounted on sleeve 311 in four circumferential positions. This permits the circumferential orientation of the base and disc 304 in the heart so that the surgeon can direct the blood in a desired direction. The number, size and type of threads can vary to achieve additional circumferential adjustment of the base relative to the sleeve.

The procedure for mitral or aortic valve replacement includes exposure of the heart through a midline sternotomy or a right anerolateral thoracotomy with subperiosteal excision of the fifth rib. Cannulas are placed within the superior and inferior venae cavae via incisions in the right atrium and are maintained there with purse string sutures. The ascending aorta or the femoral artery is used for arterial return flow via another catheter. Ventricular fibrillation is induced electrically before the left atrium is opened to prevent air embolization. A longitudinal left atriotomy allows visualization of the chamber and the mitral valve area. The diseased valve is carefully excised and calcium is removed from the valve's annulus and from the outflow track. As shown in FIG. 8, a small annular valvar rim or remnant 59 is retained for accommodating sutures 58 of the suture assembly 26. As shown in FIG. 9, suture assembly 26 is secured to the heart tissue with suitable sutures 58 with the valve 25 removed from the suture assembly 26. After the suture assembly 26 is secured to the heart tissue, the valve 25 is attached to the suture assembly. This is shown in FIG. 10 and is accomplished by rotating the base 33 relative to the sleeve 48. A turning tool having a handle and fingers is used to apply rotational force on base 33. The fingers can project into holes in the top or inflow side of the base 33 or can engage the legs and pivot structures so that rotational force can be applied to base 33. The threaded sections 46 and 51 cooperate with each other to connect base 33 to the sleeve 48. When base 33 is fully on sleeve 48, the shoulders 47 and 52 abut against each other. The top of base 33 is in alignment with the top of the flange 53. In a similar manner, the bottom of base 33 is in alignment and flush with the outer surface of flange 54. The lock mechanism 64 is then actuated to hold the base in its assembled position relative to sleeve 48. This is accomplished by rotating the body 67 with a tool. The tool fits into the socket 71 so that the head 68 can be rotated to a locked position, as shown in full lines in FIG. 6. The left atriotomy is then closed and the heart is rewarmed. The heart is defibrillated with AC or DC current, unless this occurs spontaneously.

In the event it is necessary to replace a heart valve prosthesis, the procedure for entering the heart is the same as described above. The heart valve prosthesis is unlocked from the sleeve 48 by rotating the lock means 64 approximately 90° or until the flat side 70 is aligned with the side of base 33, as shown in FIG. 3. This is accomplished by insertion of a tool in socket 71 and rotating the tool. The valve base 33 is now rotated with the turning tool in a release direction, thereby separating the valve base 33 from the sleeve 48. A new valve can then be inserted into the sleeve 48 and attached thereto. This is accomplished by rotating the base until the base of the new valve is in alignment with the sleeve 48, as shown in FIG. 4. The lock mechanism 64 is then rotated with the tool to the locked position, as shown in FIG. 5, thereby holding the base 33 in its position relative to sleeve 48.

The heart valve prosthesis and suturing assembly and method of implanting the heart valve prosthesis and suturing assembly have been shown and described with respect to several embodiments of the invention. Changes, modifications, and substitutions of materials, structure and methods can e made by those skilled in the art without departing from the invention.

The embodiments of the invention in which an exclusive property or privilege is claimed are defined as follows:

1. A heart valve prosthesis and suturing means adapted to be attached to heart tissue and support the heart valve prosthesis in the heart comprising: an annular base having a passage for carrying blood, said base having a cylindrical outside wall, an outside threaded section and an outside shoulder between the outside wall and the outside threaded section, valving means movable relative to the base to a first position to allow blood to flow in one direction through the passage and to a second position to restrict the flow of blood through the passage in the direction opposite the one direction, means retaining the valving means in operative movable relation with the base, suturing means attachable to heart tissue, said suturing means including a sleeve having a cylindrical inside wall, an inside threaded section and an inside shoulder between the inside wall and inside threaded section, said inside and outside walls, threaded sections and shoulders engaging each other when the base is mounted on the sleeve, said sleeve having an outside annular channel, a suturing collar located in the channel adapted to be secured to heart tissue, and releasable lock means mounted on the sleeve and engageable with the base to fix the position of the base on the sleeve, said lock means having a lock position to fix the location of the base on the sleeve and a release position allowing the heart valve prosthesis to be mounted on and removed from the suturing means after the suturing means is attached to the heart tissue.

2. The structure of claim 1 wherein: the lock means has a body and means to hold the body in assembled relation with the sleeve whereby the lock means is retained on the sleeve in both the lock position and release position of the lock means.

3. The structure of claim 1 wherein: said inside and outside threads have a plurality of starts.

4. The structure of claim 1 wherein: the lock means comprises a body located in a bore in the sleeve, a head attached to the body, said head having a portion engageable with the base when the base is mounted on the sleeve, and means engageable with the body and sleeve to hold the body in assembled relation with the sleeve whereby the lock means is retained on the sleeve in both the lock position and release position of the lock means.

5. The structure of claim 1 wherein: the suturing collar includes a porous fabric and means holding the fabric on the sleeve.

6. The structure of claim 5 wherein: the sleeve has grooves open to the channel for accommodating parts of the fabric, and said means holding the fabric on the sleeve includes cord means holding the parts of the fabric in the grooves.

7. The structure of claim 1 wherein: the valving means is a ball.

8. The structure of claim 1 wherein: the valving means is a disc.

9. The structure of claim 1 wherein: the valving means is a discoid valve poppet.

10. The structure of claim 1 wherein: the valving means is a member that moves angularly relative to the base.

11. Means for supporting a heart valve prosthesis in a heart, said heart valve having a base, said base having a passage for carrying blood, valving means for controlling one-way flow of blood through the passage, and means retaining the valving means in moving operative relation with the base comprising: first means attachable to heart tissue, second means associated with the first means and a base to releasably support the base on the first means whereby the heart valve prosthesis can be mounted on and removed from the first means after the first means is attached to the heart tissue, and lock means mounted on the first means, said lock means movable to a release position to allow the heart valve prosthesis to be removed from and mounted on the first means and movable to a lock position to hold the heart valve prosthesis in a fixed position relative to the first means.

12. The means of claim 11 wherein: the first means includes an annular sleeve and the second means includes means on the sleeve for releasably attaching the base to said sleeve.

13. The means of claim 11 wherein: said second means comprises screw threads.

14. The means of claim 11 wherein: said lock means has a body and means to hold the body in assembled relation with the first means when the lock means is in either the release position or the lock position.

15. The means of claim 11 wherein: the first means includes an annular sleeve, a collar surrounding the sleeve, said collar including a porous fabric and means holding the fabric on the sleeve.

16. The means of claim 11 wherein: the second means includes first screw threads on the base and second screw threads on the first means, said first and second threads cooperating with each other to hold the base on the first means.

17. The means of claim 16 wherein: the first and second screw threads have a plurality of starts.

18. A suturing assembly attachable to heart tissue for releasably holding a heart valve prosthesis, comprising: an annular member having means for releasably holding the heart valve prosthesis cover means surrounding the annular member, means holding the cover means on the annular member and lock means movably mounted on the annular member locatable in a release position to allow the heart valve prosthesis to be mounted on and removed from the annular member and locatable in a lock position to hold the heart valve prosthesis in a fixed position relative to the annular member.

19. The suturing assembly of claim 18 wherein: the means for releasably holding the heart valve prosthesis includes screw threads cooperating with a portion of the heart valve prosthesis.

20. The suturing assembly of claim 19 wherein: the threads have a plurality of starts.

21. The suturing assembly of claim 18 wherein: the annular member has outwardly directed flanges and grooves adjacent said flanges, said cover means having portions located in the grooves, said means holding the cover means including cord means holding the portions in the grooves.

22. The suturing assembly of claim 18 wherein: the annular member is a sleeve, said means for releasably holding the heart valve prosthesis comprising thread means on part of the sleeve that cooperate with portions of the heart valve prosthesis to releasably hold the heart valve prosthesis in assembled relation with the sleeve.

23. The suturing assembly of claim 18 wherein: the lock means has a body and means to hold the body in assembled relation with the annular member when the lock means is in either the release position or the lock position.

24. The suturing assembly of claim 18 wherein: the heart valve prosthesis has a base with a cylindrical outside wall, a threaded section and a shoulder between the outside wall and threaded section, said annular member including a cylindrical inside wall, a threaded section, and a shoulder between the inside wall and threaded section, said inside and outside walls, threaded sections and shoulders engaging each other when the heart valve prosthesis is mounted on the suturing assembly.

25. A method of implanting a heart valve prosthesis and suturing assembly in a heart, said prosthesis having a base and said suturing assembly having a sleeve accommodating the base, coacting means on the base and sleeve to mount the base on the sleeve, and releasable lock structure movable to a lock position to hold the base on the sleeve and movable to a release position to allow the base to be mounted on the sleeve, comprising: exposing the heart, opening the exposed heart, removing the defective natural heart valve, placing the suturing assembly in the opening formed by the removed natural heart valve, attaching the suturing assembly to the heart tissue with the lock structure located in the release position, attaching the heart valve prosthesis to the suturing assembly by positioning the base in assembled relation with the sleeve, moving the lock structure to the lock position to fix the position of the base on the sleeve, and closing the heart.

26. The method of claim 25 wherein: the suturing assembly is attached to the heart tissue with stitches.

27. The method of claim 25 including: circumferentially orientating the heart valve prosthesis on the suturing assembly when the heart valve prosthesis is being attached to the suturing assembly.

28. A method of replacing a first heart valve prosthesis located in a heart with a second heart valve prosthesis in a suturing assembly attached to heart tissue without removing the suturing assembly from the heart tissue, each prosthesis having a base, said suturing assembly having a sleeve accommodating each base, coacting means on each base and the sleeve to mount each base on the sleeve, and releasable lock structure movable to a lock position to hold each base on the sleeve and movable to a release position to allow each base to be mounted on and removed from the sleeve, comprising: exposing the heart, opening the exposed heart, moving the lock structure to the release position, removing the first heart valve prosthesis from the suturing assembly without separating the suturing assembly from the heart tissue, mounting the second heart valve prosthesis on the suturing assembly by positioning the base of the second heart valve prosthesis in assembled relation with the sleeve, moving the lock structure to the lock position to fix the position of the base of the second heart valve prosthesis on the sleeve, and closing the heart.

29. The method of claim 28 including: circumferentially orientating the second heart valve prosthesis on the sleeve when the second heart valve prosthesis is being mounted on the sleeve.

30. A heart valve prosthesis and suturing means adapted to be attached to heart tissue and support the heart valve prosthesis in the heart comprising: a heart valve prosthesis having an annular base having an inside wall forming a passage for carrying blood and an outside wall, valving means movable relative to the base to a first position to allow blood to flow in one direction through the passage and movable to a second position to restrict the flow of blood through the passage in the direction opposite the one direction, means retaining the valving means in operative movable relation to the base, suturing means attachable to heart tissue, said suturing means including a sleeve having an inside wall and means surrounding the sleeve attachable to heart tissue, coacting means on the outside wall of the base and the inside wall of the sleeve to releasably mount the base on the sleeve whereby the heart valve prosthesis can be mounted on and removed from the suturing means after the suturing means is attached to the heart tissue, and releasable lock means cooperating with the sleeve and the base to hold the base on the sleeve, said lock having a lock position to fix the location of the base on the sleeve and a release position allowing the base to be mounted on and removed from the sleeve.

31. The structure of claim 30 wherein: said lock means has a body and means to hold the body in assembled relation with the sleeve whereby the lock means is retained on the sleeve in both the lock position and the release position of the lock means.

32. The structure of claim 30 wherein: the lock means comprises a body located in a bore the sleeve, a head attached to the body, said head having a portion engageable with the base when the base is mounted on the sleeve, and means engageable with the body and sleeve to hold the body in assembled relation with the sleeve whereby the lock means is retained on the sleeve in both the lock position and release position.

33. The structure of claim 30 wherein: the coacting means includes an outside threaded portion on the base and an inside threaded portion on the sleeve, said inside and outside threaded portions cooperating with each other to mount the base on the sleeve.

34. The structure of claim 33 wherein: said inside and outside threaded portions have threads with a plurality of starts.

35. The structure of claim 30 wherein: the base has a cylindrical outside wall, said sleeve has a cylindrical inside wall adapted to engage the outside wall of the base when the base is mounted on the sleeve, said outside wall of the base and inside wall of the sleeve including cooperating shoulders which engage each other when the coacting means cooperates to mount the base on the sleeve.

* * * * *

UNITED STATES PATENT AND TRADEMARK OFFICE
CERTIFICATE OF CORRECTION

PATENT NO. 3,997,923
DATED      December 21, 1976
INVENTOR(S) ZINON C. POSSIS

It is certified that error appears in the above–identified patent and that said Letters Patent are hereby corrected as shown below:

Col.2, line 7, delete "valve" and insert --valving--.

Col.2, line 18, before "heart tissue" delete "the".

Col.3, line 38, "ventricle 22. the" should read --ventricle 22.  The--.

Col.3, line 60, after "wall" delete "44" and insert --42--.

Col.5, line 53, after "100 is" insert --a--.

Col.9, line 9, after "can" delete "e" and insert --be--.

Claim 11, Col. 10, line 13, after "and" delete "a".

Claim 18, Col. 10, line 48, after "heart valve prosthesis", insert -- , --.

Claim 30, Col. 12, line 31, after "said lock" insert --means--.

Signed and Sealed this

Fifteenth Day of March 1977

[SEAL]

Attest:

RUTH C. MASON
*Attesting Officer*

C. MARSHALL DANN
*Commissioner of Patents and Trademarks*